Figure 1:
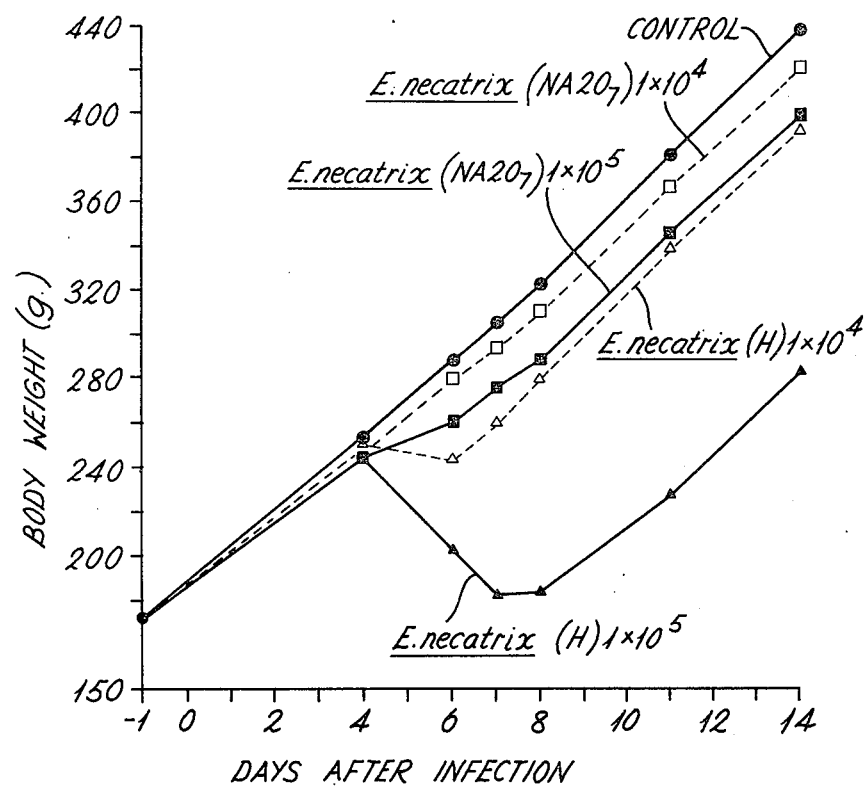

United States Patent [19]

Shirley

[11] 4,438,097

[45] Mar. 20, 1984

[54] COCCIDIOSIS VACCINES

[75] Inventor: Martin W. Shirley, Huntingdon, England

[73] Assignee: National Research Development Corporation, London, England

[21] Appl. No.: 299,922

[22] Filed: Sep. 8, 1981

[30] Foreign Application Priority Data

Sep. 5, 1980 [GB] United Kingdom ................ 8028676

[51] Int. Cl.$^3$ .......................................... A61K 39/012
[52] U.S. Cl. ....................................... 424/88; 424/93; 435/258
[58] Field of Search ..................... 424/88, 93; 435/258

[56] References Cited

U.S. PATENT DOCUMENTS

| 3,029,282 | 4/1962 | Toy et al. | 260/543 |
|---|---|---|---|
| 3,864,394 | 2/1975 | Via et al. | 260/543 P |
| 4,241,021 | 12/1980 | Skrzec | 422/143 |

OTHER PUBLICATIONS

T. A. Shibalova, vol. IX, pp. 299–303, (1972), "Acta Protozoologica".

P. L. Long, "The Growth of Eimeria in Cultured Cells and in Chicken Embryos" Symp. Proceedings, Ontario, (1974).

D. J. Doran, Journ. of Parasitology, vol. 57, No. 5, Oct. 1971, "Survival and Development of Five Species of Chicken Coccidia in Primary Chicken Kidney Cell Cultures".

P. L. Long, Parasitology, 56, pp. 575–581, (1966), "The Growth of Some Species of Eimeria in Avian Embryos".

*Primary Examiner*—Thomas G. Wiseman
*Assistant Examiner*—Frederick W. Pepper
*Attorney, Agent, or Firm*—Oblon, Fisher, Spivak, McClelland & Maier

[57] ABSTRACT

Attenuated *E. necatrix* suitable for use in the production of a live vaccine is produced by passaging pathogenic *E. necatrix* in embryonated eggs for a sufficient number of passages i.e. from about 20 up to about 50 or more egg passages. The live egg-attenuated *E. necatrix* of the invention may be formulated in vaccines, e.g. feed or drinking water vaccines, for prevention and control of coccidiosis in poultry, usually with other strains of *Eimeria* (i.e. *E. acervulina, E. brunetti, E. maxima, E. mivali, E. praecose* and *E. tenella*) as live pathogenic strains thereof or preferably attenuated non-pathogenic lines thereof. In a preferred embodiment the egg-attenuated *E. necatrix* of the invention is formulated in a vaccine comprising attenuated, precocious *E. acervulina*.

11 Claims, 3 Drawing Figures

COCCIDIOSIS VACCINES

This invention relates to coccidiosis vaccines, and in particular to vaccines for preventing and combatting coccidiosis in poultry.

Coccidiosis is a disease of animals and birds caused by protozoal parasites called coccidia. In many cases, under natural environmental conditions, this disease is relatively benign; though with domesticated animals infections can be severe especially in poultry where the use of intensive rearing conditions favours the reproduction of the parasites. Coccidiosis of poultry is caused by coccidia belonging to the genus Eimeria which invade the tissue of the intestinal tract where some species of the parasite may cause haemorrhage, all species may cause weight loss and in the case of severe infection most may cause death. Thus the prevention and control of this disease is of great commercial importance in the chicken and egg production industries.

Anticoccidial drugs are widely used to prevent and combat the disease of coccidiosis in poultry, the drugs normally being given to the birds together with their feed. The use of anticoccidial drugs is not altogether satisfactory, however, in view of expense and also effectiveness which is limited by emergence of drug resistant strains of coccidia requiring a continued search for new effect anti-coccidial agents and the attendant expense of meeting national safety and efficacy regulations.

Coccidiosis of chickens is caused by seven main species of Eimeria parasites: *E. acervulina, E. brunetti, E. maxima, E. mivati, E. praecox, E. necatrix* and *E. tenella;* the coccidia undergoing and completing a complex life cycle in the tissues of the intestinal tract of the chicken. The first invasive forms of the parasite are sporozoites which are released from sporocysts derived from sporulated oocysts, the coccidia then passing through a number of asexual multiplicative phases (schizogony) having merozoite invasive forms and culminating in a sexual reproductive phase (gametogony) giving rise to oocysts which are passed from the bird with faecal material and which, on becoming infective (sporulated), act as a source of further infection.

In view of the inherent disadvantages of anticoccidial drugs mentioned previously attempts have been made to develop vaccines to protect poultry against coccidial infection. Hitherto, these vaccines have generally been based upon low doses of live, pathogenic organisms, and thus are not wholly desirable as it is possible that the vaccine itself can give rise to field cases of coccidiosis. More recently, some species of Eimeria parasites, namely *E. mivati* and *E. tenella,* have been attenuated in embryonated eggs, and thus there now exists a limited possibility of preparing a vaccine from live, attenuated, non-pathogenic organisms. Unfortunately, however, immunity is species specific and the attenuation of all Eimeria species is necessary for production of a fully effective attenuated coccidiosis vaccine. Moreover, attempts to attenuate other species of Eimeria, including *E. maxima, E. brunetti* and especially the highly pathogenic species *E. necatrix,* have proved unsuccessful, *E. necatrix,* appearing to be capable of completing the sexual reproductive stages of its life cycle only in the natural host, the chicken. Growth of *E. necatrix* through its whole life cycle in embryonated eggs was reported some time ago (Shibalova, Acta Protozoologica, Warszawa, 1972, Volume IX, fasc. 19, pages 299–303), but subsequent attempts to repeat this work have proved completely unsuccessful (P. L. Long, "The growth of Eimeria in cultured cells and in chicken embryos: a review", Proceedings of the Symposium on Coccidia and Related Organisms, Ontario 1974 page 63), and it had not been generally accepted that *E. necatrix* can be propagated through its complete life cycle in embryonated eggs.

It has now been found, contrary to expectation, that *E. necatrix* can be propagated throughout its complete life cycle in embryonated eggs, and further that repeated passaging of this organism in embryonated eggs leads to attenuation of the parasite.

Accordingly the present invention comprises a process in which pathogenic *E. necatrix* is passaged in embryonated eggs for a sufficient number of passages to produce an attenuated strain of *E. necatrix* suitable for use in the production of a live, attenuated vaccine.

Thus, the invention also includes egg attenuated strains of *E. necatrix* suitable for use in live attenuated vaccines.

Furthermore the invention includes vaccines, processes for the production of vaccines and methods of preventing and controlling coccidiosis in poultry using attenuated strains of *E. necatrix* according to the invention.

Eggs from any suitable breed of chicken may be used for attenuation of *E. necatrix* according to the invention, and in particular attenuation is carried out in the chorioallantoic membrane (CAM) of embryonated eggs. It has been found that eggs of some breeds of chickens appear to give better yields of parasite oocysts than eggs of other breeds. Thus, for instance, embryonated Rhode Island Red (RIR) eggs appear to give increased yields of oocysts as compared with Brown Leghorn (BrL) eggs.

Generally also, any suitable in ovo culture conditions may be employed during attenuation of *E. necatrix.* Advantageously, however, it has been found that relatively elevated temperatures, e.g. temperatures of about 41° C., e.g. 39°–43° C., are desirable for growth of *E. necatrix* in embryonated eggs. Furthermore, it has been found that regular turning of eggs, e.g. a minimum of at least once or twice a day, is desirable during propagation in the CAM, and for example, an automatic incubation facility which automatically turns the eggs about 48 times during the course of one day has been found to give highly successful results.

Embryonated eggs may be inoculated with sporozoites of *E. necatrix* and oocysts subsequently recovered from the eggs, usually from the urate and other debris present in the allantoic fluid. Initially it may be desirable to use relatively high doses of sporozoites, usually about $1\times10^5$ sporozoites or more per egg, e.g. from $1\times10^5$ up to $1\times10^7$ sporozoites per egg, to establish an egg-adapted strain, though subsequently, e.g. after about 13–14 passages, lower doses, e.g. about $5\times10^4$ sporozoites or less per egg, are generally required. Also it may be desirable, particularly during the initial stages of passaging e.g. for about the first 6–10 egg passages, to carry out alternate passages in eggs and chickens so as to obtain a reasonable yield of oocysts. Harvesting of oocysts may be carried out after a suitable period of incubation for each passage, usually at least 6 or 7 days after inoculation, though preferably after a longer period, e.g. about 7–8 days. Relatively short incubation periods, e.g. 6 or 7 days or even as little as 5 days in some cases, may be used when selection for precocious development is imposed on the parasite during passaging. During the earlier passages, however, longer periods of incubation, e.g. about 8 days, are desirable to obtain satisfactory yields of oocysts, and such longer incubation periods may also be used during later stages of passaging to obtain enhanced oocyst yields.

Typically passaging is continued for a sufficient number of passages to produce a non-pathogenic strain of *E. necatrix* of suitable immunogenicity and stability for use in a live attenuated vaccine. In this regard, *E. necatrix* appears to behave anomalously on passaging when compared with other species of Eimeria, e.g. *E. tenella*, which have been previously attenuated by passaging in eggs. It has been found that in parallel with loss of pathogenicity on passaging immunogenicity also decreased, and furthermore that stability has not yet become a genetically stable trait at the stage at which useful immunogenicity still remains. Thus an attenuated strain of *E. necatrix* according to the invention represents an acceptable compromise between the opposing tendencies of decreasing immunogenicity as against increasing stability, coupled with non-pathogenicity.

It has been found in accordance with the present invention that from about 20 up to about 50 passages or more are required to produce a strain of *E. necatrix* suitable for use in a live attenuated vaccine. For instance, up to about 50 or 60 egg passages may be used when selection pressures such as selection for precocious development are relaxed during passaging; though under such relaxed selection conditions, from about 30 up to about 50 passages are normally required, preferably from about 35 to about 39 passages. Alternatively when selection pressures, such as selection for precocious development, are imposed, as specifically described hereinafter, normally from about 20 up to about 40 passages, preferably from about 25 up to about 35 passages, or especially from about 28 up to about 33 passages are used.

The attenuated strains of the invention are characteristically altered with respect to the parent pathogenic strain by the passaging procedure and may be distinguished therefrom in terms of pathogenicity and adaptation to growth in eggs.

Thus attenuated strains of the invention typically do not cause death when administered to susceptible chickens, e.g. at doses of about $5 \times 10^4$ of fresh oocysts per chicken. Preferably also, the attenuated strains cause only relatively minor changes to the gross appearance of the intestine on infection, and especially cause no actual weight loss (weight loss being determined on a group basis) when administered to chickens at doses of about $5 \times 10^4$ of fresh oocysts per bird.

Additionally, the attenuated strains are typically of stability such that they are of reduced pathogenicity when compared with the parent pathogenic strain, after they have undergone at least 5, e.g. 5 or 6, or especially 10, consecutive chicken passages after attenuation and before administration to the susceptible chickens. Thus, for example an attenuated strain, attenuated by 29 passages in eggs followed by 6 consecutive passages in chickens, causes less than 50%, e.g. 30%, mortality in chickens at a dose of $5 \times 10^4$ oocysts per chicken, compared with 100% mortality caused by the same dose of the pathogenic parent strain.

Thus, it will be appreciated that strains of *E. necatrix* attenuated according to the invention even after subsequent passaging in chickens are more advantageous, from the point of view of pathogenicity, for vaccine use than the parent pathogenic strains. Typically also the attenuated strains provide reasonable protection against subsequent challenge with virulent *E. necatrix*. Thus, attenuated strains usually provide at least 85% and preferably at least 95% protection against challenge with virulent *E. necatrix*, for example, as reckoned by a procedure in which immunised and non-immunised birds are given a small challenge of virulent organisms and the resultant output of oocysts in the immunised and non-immunised birds are compared.

Generally also attenuated strains according to the invention typically reproduce in chickens less readily, though grow in eggs more easily, than the parent pathogenic strains. Thus, for example, a $5 \times 10^3$ dose of oocysts of the parent strain produces a yield of about $25 \times 10^6$ oocysts in chickens whereas a $25 \times 10^3$ dose of an attenuated strain after 29 egg passages produces only about $1 \times 10^6$ oocysts, and after 36 egg passages produces only about $0.4 \times 10^6$ oocysts. Conversely, as regards growth in eggs, for example, a $10^5$ dose of sporozoites of the parent pathogenic strain per egg gave a yield of only $3 \times 10^3$ oocysts after 8 days incubation; whereas a $2.2 \times 10^4$ dose of sporozoites per egg of a strain attenuated by 29 egg passages gave a yield of $560 \times 10^3$ oocysts after only 6 days incubation.

Attenuated non-pathogenic strains of *E. necatrix* according to the invention may be formulated as desired into vaccines for prevention and control of coccidiosis in poultry. Attenuated *E. necatrix*, which may be in the form of sporocysts, though is usually in the form of oocysts, may be formulated into vaccines with other strains of Eimeria including live pathogenic strains of Eimeria such as *E. maxima*, *E. acervulina* and *E. brunetti*, usually as low doses thereof, and/or preferably other attenuated non-pathogenic strains of Eimeria such as *E. tenella* and *E. mivati*. Such combined coccidiosis vaccines preferably contain, in addition to attenuated *E. necatrix*, strains of all the major coccidia of poultry, i.e. *E. acervulina*, *E. brunetti*, *E. maxima*, *E. mivati* and *E. tenella*, preferably as attenuated strains thereof, and may also contain strains of *E. praecox* to provide a fully effective vaccine for use against coccidiosis of poultry.

In preferred embodiments vaccines according to the present invention comprise, in addition to egg attenuated *E. necatrix*, egg attenuated *E. tenella* and/or egg attenuated *E. mivati*, and/or *E. acervulina* attenuated by selection for precocious development in the chicken. In addition or alternatively *E. tenella*, and possibly also *E. mivati*, may be attenuated by selection for precocious development in the chicken. Vaccines according to the invention may also comprise low doses of pathogenic *E. maxima*, this species being highly immunogenic and therefore requiring only a low dose for effective protection.

Vaccines according to the invention may also comprise antigenic material from other species of organisms besides Eimeria, such as viruses.

The vaccines of the invention may be in any suitable form for administration to poultry including those forms in which coccidiosis vaccines have been provided in the past, e.g. COCCIVAC. Vaccine is typically in the form of a suspension of oocysts or sporocysts, normally a suspension in a sterile aqueous medium, which may contain suspending agents such as gelatin. Oocysts or sporocysts may be pretreated prior to vaccine formulation; for instance, treated with an agent e.g. hypochlorite or "Chlorox", to render the oocysts more readily infective e.g. for use with young birds. The vaccine may be administered to birds by intravenous or intraperitoneal injection, but this is generally an inefficient ultilisation of the vaccine and vaccine is preferably administered by mouth. For instance, vaccine may be given individually by mouth in the form of graded doses of oocysts, e.g. up to about $5 \times 10^3$ oocysts of each strain per bird, though such individual vaccination is normally only economically feasible for vaccination of layer, replacement and breeder birds. In preferred methods for vaccination of broiler chickens, oocysts are given to the chickens together with their feed, e.g. in bulk feed or in a feed concentrate alternative, or drinking water. Feed and drinking water vaccination may be carried out by administering small doses of oocysts, e.g. $10-10^3$ oocysts of each strain per day, over an extended period of time, e.g. 1-5 weeks. Alternatively drinking water vaccination may be carried out by giving the birds one or two larger doses of about $5 \times 10^3$ oocysts e.g. from about $5 \times 10^2$ up to about $5 \times 10^4$ oocysts, of each strain per bird. Such feed and drinking water vaccines may be made from concentrated stock vaccine preparations, usually comprising aqueous suspensions of oocysts.

The present invention is concerned with the preparation of a "live" vaccine, and thus it will be appreciated that the attenuated strains or the vaccine itself may be used as a seed material for production of oocysts or sporocysts, preferably by propagation in eggs, for use in vaccine. Thus the invention includes per se attenuated strains of *E. necatrix* produced by the method of the invention. Birds may be vaccinated at any suitable age, and are usually at least 3 days old before first vaccination, though it may be possible to vaccinate as early as one day old if sporozoites are used. When two doses of vaccine are used, the first is normally given when the birds are 3 days to a week old and subsequently after a further 1-10 weeks dependent upon the type of bird being vaccinated.

Generally also the birds are preferably maintained under conditions which permit them access to their litter allowing reinfection with oocysts derived from the vaccine, and thereby advantageously increasing the level of immunological protection. For example, the litter may be dampened periodically to assist sporulation of the oocysts.

It will be appreciated from the foregoing that the present invention is primarily concerned with processes for attenuation of pathogenic *E. necatrix* by passaging in embryonated eggs, advantageously to provide live attenuated *E. necatrix* vaccines for protection of poultry. In as far, however, as the live attenuated strains of *E. necatrix* produced on passaging are new organisms produced by human intervention from the parent pathogenic strain, the present invention also concerns new and useful organisms. Thus, for better exemplification of the invention, samples of representative attenuated strains of *E. necatrix* have been deposited with the Central Veterinary Laboratory, Weybridge, Surrey, England, a U.K. Government laboratory having extensive experience of maintaining cultures of poultry parasites, including coccidia. Cultures of strains of *E. necatrix* attenuated by 21, 32 and 48 egg passages were deposited with the Central Veterinary Laboratory on the 21st August 1980 and are identified as strains L/5B/G/21, L/5B/G/32 and L/5B/G/48 respectively, and also as strains B3/6/R/21, B3/6/R/32 and B3/6/R/48 respectively. These and other attenuated strains of *E. necatrix* of the invention exhibit the typical characteristics of coccidia of species *E. necatrix,* though having pathogenicity and adaptation of growth in eggs altered as herein described with respect to the parent pathogenic strain.

The invention is further described by way of illustration only in Examples 1 and 2 which relate to the attenuation of *E. necatrix* in embryonated eggs and refer to the accompanying diagrams:

FIG. 1 which is a graph comparing body weight gains of chickens after infection with parent pathogenic organisms with those of chickens infected with organisms attenuated by 20 chicken passages, and FIG. 2 which is a similar graph comparing strains attenuated by 36 egg passages, and 29 egg passages plus 6 consecutive chicken passages with the fully pathogenic parent strain.

Example 3 is included to describe a method, as yet unpublished, for attenuating *E. acervulina* by selection for precocious development in the chicken and refers to FIG. 3 which is a graph comparing body weight gains of chickens after infection with the parent pathogenic strain of *E. acervulina* (H) with those of chickens infected with the attenuated, precocious line of *E. acervulina* (HP).

EXAMPLE 1

The Houghton (H) strain of *E. necatrix* isolated at Houghton in December 1956 and described by Horton-Smith and Long (Journal of Comparative Pathology and Therapeutics (1959), 77, 315–325) was used as the starting material in the production of an attenuated strain of *E. necatrix* according to the invention.

Sporozoites were obtained as described by Long (Journal of Comparative Pathology (1972), 82, 439–445) and were inoculated into the allantoic cavity of eggs by the method of Long (Journal of Comparative Pathology (1972), 82, 429–437).

In a preliminary experiment, thirty 10-day-old embryonating Brown Leghorn (BrL) eggs given $1.3\times10^5$ sporozoites of *E. necatrix* (H) were examined for oocysts 6, 7 and 8 days after inoculation. In one egg examined on the sixth day no oocysts were found, but an average of $2.5\times10^3$ oocysts was recovered from each of 9 eggs on the seventh day. At 190 h the urate of the remaining 20 eggs was examined and a total of $0.39\times10^6$ oocysts were recovered. These oocysts sporulated and were subsequently inoculated into 3-week-old Light Sussex (LS) chickens to confirm the identity of the parasites recovered from eggs as *E. necatrix.*

The embryonating eggs used in the above and subsequent experiments were maintained at 37° C. for the first 10 days of incubation and after inoculation at this time with sporozoites the temperature was raised to 41° C. Similarly occysts were recovered from eggs 6, 7 or 8 days after inoculation using the trypsin-digest method described by Long in the second of the above mentioned Journal of Comparative Pathology publications.

Serial Passage

A dose response experiment in which eggs were inoculated with 0.5, 1, 2 or $3\times10^5$ sporozoites indicated that the optimum dose with regard to yield of oocysts was $1\times10^5$. Yields were consistently poor, however, even with this dose and in order to establish an egg-adapted line it was found necessary initially to carry out alternate egg and chicken passages, up to the first eight egg passages. Replacement of BrL eggs by RIR eggs, and turning of the eggs in the incubator, however, was found to increase the number of oocysts recovered on the eighth day after inoculation. In view of this improvement the inoculum of sporozoites was reduced to about $6 \times 10^4$ sporozoites per egg by the sixteenth passage.

Initially very few oocysts appeared in the urate by the seventh day and it was found necessary to continue incubation until after the eighth day to obtain sufficient parasites for further passages. Oocysts recovered at this time sporulated well and sporulation rates between 80 and 90% were usual.

Little mortality due to coccidiosis was observed throughout the passages, although some deaths occurred between 4 and 6 days after inoculation. These, and other data which summarise the development of *E. necatrix* during the first twenty passages in eggs, are given in Table 1 below.

With the apparent step-wise improvement in yield of oocysts particularly between the eighth and fourteenth passage, it became possible thereafter to recover sufficient parasites 7, and even 6 days after inoculation and to impose upon the parasite a more severe selection for egg-adaptation.

TABLE 1

| The reproduction of *E. necatrix* in eggs during serial passage | | | | |
|---|---|---|---|---|
| Passage Number | Breed of egg used | Number sporozoites given/egg ($\times 10^{-3}$) | Day after inoculation when oocysts harvested | Oocysts recovered/ egg ($\times 10^{-3}$) | Mortality (%) |
| $1_0$ | BrL | 100 | 8 | 3 | 0 |
| $2_1$ | BrL | 50 | 8 | 3 | 0 |
| $3_2$ | BrL | 100 | 8 | 2 | 7 |
| $4_3$ | BrL | 100 | 8 | 12 | 19 |
| $5_3$ | BrL | 50 | 8 | 3 | 0 |
| $6_4$ | BrL | 100 | 8 | 2 | 0 |
| $6_4$ | BrL | 150 | 8 | 10 | 15 |
| $6_4$ | BrL | 200 | 8 | 4 | 5 |
| $7_6$ | BrL | 110 | 8 | 4 | 5 |
| $7_6$ | RIR | 110 | 8 | 65 | 2 |
| $8_7$ | RIR | 90 | 8 | 40 | 1 |
| $8_7$ | RIR | 45 | 8 | 7 | 0 |
| $9_7$ | RIR | 90 | 8 | 56 | 1 |
| $10_7$ | RIR | 110 | 8 | 450 | 7 |
| $11_7$ | RIR | 100 | 8 | 340 | 0 |
| $12_7$ | RIR | 85 | 8 | 115 | .5 |
| $13_7$ | RIR | 100 | 8 | 910 | 2 |
| $14_7$ | RIR | 100 | 8 | 1,300 | 0 |
| $14_7$ | RIR | 50 | 8 | 730 | 0 |
| $14_7$ | RIR | 100 | 7 | 850 | 0 |
| $15_7$ | RIR | 100 | 7 | 750 | 1 |
| $16_7$ | RIR | 85 | 6 (140h) | 10 | 2 |
| $17_7$ | RIR | 65 | 7 | 1,280 | 0 |
| $18_7$ | RIR | 55 | 6 (140h) | 10 | 0 |
| $19_7$ | RIR | 53 | 7 | 1,330 | 0 |
| $20_7$ | RIR | 52 | 7 | 840 | 0 |

The numerical code used to indicate passage number in Table 1 comprises a main number indicating the number of egg passages and a subscript number indicating the number of chicken passages used, and is employed elsewhere in the description. Thus *E. necatrix* NA $20_7$ indicates an egg-adapted line of *E. necatrix* which has undergone 20 passages including initially 7 intermittent passages in chickens.

Effect of *E. necatrix* (H) and *E. necatrix* (NA $20_7$) on the body weight gain of 3-weeks-old LS chickens and lesion scores Body weight gain For this experiment five groups each consisting of three sub-groups of ten chickens were used. Group 1 was given $1 \times 10^4$ oocysts of *E. necatrix* (NA $20_7$); group 2 was given $1 \times 10^4$ oocysts of *E. necatrix* (H); group 3 was given $5 \times 10^4$ oocysts of *E. necatrix* (NA $20_7$) and group 4 was given $5 \times 10^4$ oocysts of *E. necatrix* (H). Group 5 was not infected. The birds were weighed individually one day before infection (D-1), and 4, 6, 7, 8, 11 and 14 days after infection. The body weights are shown in the accompanying diagram FIG. 1, each value given being the mean determined from observations on the 30 chickens (or survivors) in each group. Details of the deaths occurring in inoculated groups (1–4) are given in Table 2 below.

TABLE 2

| Pathogenicity of *E. necatrix* (NA $20_7$) and *E. necatrix* (H): Summary of mortality | | | | | | | | | |
|---|---|---|---|---|---|---|---|---|---|
| Parasite and dose of oocysts given | Number of birds | Percentage mortality | Days after infection on which deaths occurred | | | | | | |
| | | | 5 | 6 | 7 | 8 | 9 | 10 | 11 |
| NA20 $1 \times 10^4$ | 30 | 0 | 0 | 0 | 0 | 0 | 0 | 0 | 0 |
| H $1 \times 10^4$ | 30 | 3 | 0 | 1 | 0 | 0 | 0 | 0 | 0 |
| NA20 $5 \times 10^4$ | 30 | 0 | 0 | 0 | 0 | 0 | 0 | 0 | 0 |
| H $5 \times 10^4$ | 30 | 40 | 2 | 5 | 3 | 2 | 0 | 0 | 1 |

The non-passaged parent strain (*E. necatrix* (H)) was found to be highly pathogenic and caused loss in body weight beginning 4 days after inoculation at both dose levels, the weight loss being greatest for the highest dose level. One chicken given $1 \times 10^4$ oocysts died, whilst 13 (40%) died in the group given $5 \times 10^4$ oocysts. In contrast no deaths occurred in the groups inoculated with the egg-adapted line and, althugh the weight gain of infected chickens was depressed with respect to the controls, there was no weight loss. From the 6th day after inoculation the growth of chickens within groups 1 and 2 was significantly different (P<0.001) from the growth of chickens in groups 3 and 4.

Lesion Scores

Twenty chickens, each given $5 \times 10^4$ oocysts of *E. necatrix* (NA $20_7$) or *E. necatrix* (H) were killed 6 days after inoculation and the intestinal lesions graded according to an arbitary scale between 0 and 4.

Grade 0 indicated no gross lesions; grade 1 presence of small scattered petechiae and white spots visible from the serosal surface; grade 2, numerous petechiae on the serosal surface and some slight ballooning of the intestine; grade 3 for extensive haemorrhage in the lumen and the presence of red or brown mucus, extensive petechiae on the serosal surface, marked ballooning of the intestine and the absence of normal intestinal contents. Grade 4 was reserved for dead birds.

Mean values obtained for the two infections were 3.2 and 1.2 for *E. necatrix* (H) and *E. necatrix* (NA $20_7$) respectively; 6 chickens given *E. necatrix* (H) died.

Immunogenicity of *E. necatrix* (NA $20_7$) and *E. necatrix* (H)

Two groups of 20, 3-weeks-old LS chickens maintained in four sub-groups of five, were given $1 \times 10^4$ oocysts of either *E. necatrix* (NA $20_7$) or *E. necatrix* (H). Twelve days later both groups, with a further group of previously uninfected chickens, were challenged with $5 \times 10^2$ oocysts of *E. necatrix* (H). Oocyst production between 6 and 13 days after inoculation was measured and the results are given below in Table 3.

TABLE 3

Cross-protection between E. necatrix (NA 20₇) and E. necatrix (H)

| Group No. | Parasite used for primary inoculation (Dose: $1 \times 10^4$ oocysts) | Total oocysts produced ($\times 10^{-6}$) per bird after challenge inoculation with $5 \times 10^2$ oocysts of E. necatrix (H) | Percent cross-protection (c.f. Group 3) |
|---|---|---|---|
| 1 | E. necatrix (NA 20₇) | 3.55 | 85.00 |
| 2 | E. necatrix (H) | 0.01 | 99.99 |
| 3 | None | 23.67 | |

Chickens given the parent strain (*E. necatrix* (H)) were almost completely protected against homologous challenge whereas those given the egg-adapted line showed 85% protection when compared with the non-immunised group challenged with *E. necatrix* (H). Two further groups of 10 chickens, similarly given a primary dose of $1 \times 10^4$ oocysts of *E. necatrix* (NA 20₇) or *E. necatrix* (H) were challenged, together with a non-immunised group, with $5 \times 10^4$ oocysts of *E. necatrix* (H). These chickens were killed after 6 days and the lesions graded. Mean lesion scores per chicken for the three groups were 2.35 (*E. necatrix* (NA 20₇)), 0.05 (*E. necatrix* (H)) and 2.80 (non-immunised controls).

EXAMPLE 2

*E. necatrix* (NA 20₇) as produced in Example 1 was passaged further in eggs up to a total of 40 egg passages. Information concerning the development of *E. necatrix* during these further twenty passages is given below in Table 4, being an extension of the information already given for the first twenty passages in Table 1, Example 1. Selection pressure for precocious development was continued during these further passages, parasites having been collected at 5 or 6 days after inoculation after the 23rd passage. It will be appreciated, however, that considerably higher yields of oocysts can be obtained if selection pressures are relaxed and oocysts recovered at a later stage after inoculation e.g. 7 or 8 days, during these and previous passages.

TABLE 4

| Reproduction of *E. necatrix* during serial passage in RIR eggs: oocysts collected 5, 6 or 7 days after inoculation of sporozoites | | | |
|---|---|---|---|
| Passage No. | No. sporozoites given per egg ($\times 10^{-3}$) | Day after inoculation when oocysts were recovered | No. oocysts recovered per egg ($\times 10^{-3}$) |
| $21_7$ | 50 | 6 | 110 |
| $22_7$ | 33 | 6 | 210 |
| $23_7$ | 29 | 5 (125–127h) | 1 |
| $24_7$ | 1 | 7 | 10 |
| $25_7$ | 4 | 6 | 140 |
| $26_7$ | 20 | 6 | 640 |
| $27_7$ | 26 | 6 | 60 |
| $28_7$ | 20 | 6 | 50 |
| $29_7$ | 22 | 6 | 560 |
| $30_7$ | 39 | 5 (125–127h) | 20 |
| $31_7$ | 44 | 5 (123–125h) | 5 |
| $32_7$ | 27 | 6 | 740 |
| $33_7$ | 23 | 5 (125–127h) | 5 |
| $34_7$ | 20 | 6 | 1,000 |
| $35_7$ | 28 | 5 (125–127h) | 20 |
| $36_7$ | 25 | 6 | 300 |
| $37_7$ | 25 | 5 (123125h) | 30 |
| $38_7$ | 20 | 5 (123–125h) | 10 |
| $39_7$ | 15 | 6 | 610 |
| $40_7$ | 8 | 6 | 980 |

The immunogenicity of the egg-adapted line was determined after a total of 22 egg passages.

Immunogenicity of *E. necatrix* (NA $22_7$) in chickens maintained in floor pen isolators Four groups of 30, 3-week-old chickens were used. Group 1 was given $1\times10^2$ oocysts of *E. necatrix* (NA $22_7$); group 2 was given $1\times10^2$ oocysts of *E. necatrix* (H) and groups 3 and 4 were not inoculated with oocysts. Six weeks later (day 41) groups 1, 2 and 3 were challenged with $5\times10^4$ oocysts of *E. necatrix* (H). Group 4 was maintained as a non-immunised, non-challenged control group. The body weights of all chickens were measured at the time of primary infection (day 0), 41 days later—at the time of challenge—and 7 days after the challenge infection (day 48). All chickens were killed at the latter time and the lesions graded.

Body weight gains of immunised chickens (groups 1 and 2) and non-immunised control chickens in group 4 were not significantly different 41 days after the primary infection as shown in Table 5 below. The body weight gain of group 3 was significantly different to that of group 1 only ($P<0.05$).

TABLE 5

| Body weight changes of chickens given *E. necatrix* and maintained in litter pen isolators | | | |
|---|---|---|---|
| Group number | Parasite used for immunisation ($1 \times 10^2$ oocysts) | Initial body weight (g) (day 0) | Weight gain number day 0 to day 41 (g) |
| 1 | *E. necatrix* (NA 22) | 197.7 | 864.5 |
| 2 | *E. necatrix* (H) | 197.7 | 814.1 |
| 3 | None | 197.7 | 785.0* |
| 4 | None | 197.3 | 802.5 |
| Group number | Challenged with $5 \times 10^4$ oocysts of *E. necatrix* (H) at day 41 | Weight gain day 41 to day 48 (g) | Mean intestinal lesion score 7 days after challenge |
| 1 | YES | 159.8 | 0 |
| 2 | YES | 158.3 | 0 |
| 3 | YES | −19.2*** | 2.2 |
| 4 | NO | 164.7 | |

***Significantly different from Groups 1, 2 and 4 ($P<0.001$)
*Significantly different from Group 1 ($P<0.05$)

Following challenge with $5\times10^4$ oocysts of *E. necatrix* (H) none of the immunised chickens died and their mean body weights (i.e groups 1 and 2) were not significantly different from that of group 4. In contrast, one chicken in group 3 died and the mean body weight was severely depressed with respect to group 4 ($P<0.001$). No coccidial lesions were seen in any of the chickens in groups 1 and 2 but a mean lesion score of 2.2 was recorded for group 3.

Stability of loss of pathogenicity of *E. necatrix* (NA $29_7$)

A preliminary experiment was conducted using two groups of 13 and one of 12, 3-weeks-old chickens. Each group was given $5\times10^4$ oocysts and group 1 received *E. necatrix* (H); group 2 received *E. necatrix* (NA $30_7$) and group 3 received *E. necatrix* (NA $29_7+1$). (The reference NA $29_7+1$ indicates that the organisms had been passaged 29 times in eggs followed by a single passage in chickens.) Six days after inoculation the chickens were killed and the intestinal lesions scored.

Mean lesion scores for the groups given *E. necatrix* (H), *E. necatrix* (NA $30_7$) and *E. necatrix* (NA $29_7+1$) were 2.62, 0 and 0.42 respectively, the overall results being given below in Table 6. Although the loss of pathogenicity of the egg-adapted line did not appear to be genetically stable, it is clear that full virulence (i.e. to that of the parent strain) was not restored. *E. necatrix* (NA 29₇+1) was passaged in chickens a further 5 times and its pathogenicity was then more critically evaluated against both the parent Houghton strain and the egg-adapted line.

TABLE 6

Lesion scores associated with infections of *E. necatrix* (H); *E. necatrix* (NA 30₇) and *E. necatrix* (NA 29 + 1)

| Parasite given | \multicolumn{9}{c}{Number of chickens showing a lesion score of:-} | | | | | | | | |
|---|---|---|---|---|---|---|---|---|---|
| | 0 | $\frac{1}{2}$ | 1 | 1$\frac{1}{2}$ | 2 | 2$\frac{1}{2}$ | 3 | 3$\frac{1}{2}$ | 4 |
| *E. necatrix* (H) | 0 | 0 | 0 | 1 | 3 | 1 | 6 | 1 | 0 |
| *E. necatrix* (NA 29 + 1) | 6 | 3 | 4 | 0 | 0 | 0 | 0 | 0 | 0 |
| *E. necatrix* (NA 30) | 13 | 0 | 0 | 0 | 0 | 0 | 0 | 0 | 0 |

Pathogenicity of *E. necatrix* (H), *E. necatrix* (NA 36₇) and *E. necatrix* (NA 29₇+6) in 3-week-old LS chickens

Body weight gain

Figure 2:
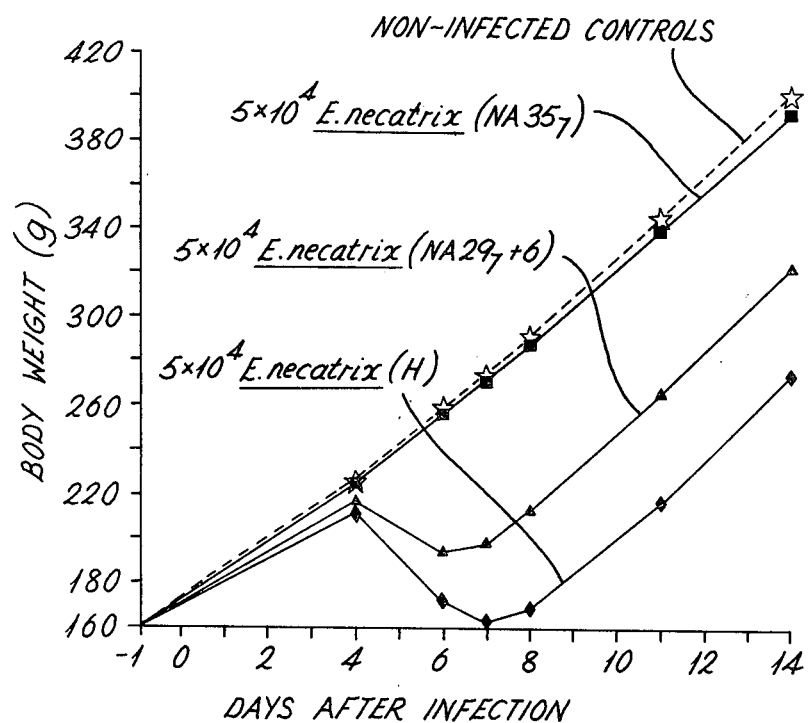

Five groups each consisting of 3 sub-groups of 10 chickens were used. Group 1 was given $5 \times 10^4$ oocysts of *E. necatrix* (NA 36₇), group 2 was given $2 \times 10^5$ oocysts of *E. necatrix* (NA 36₇), group 3 was given $5 \times 10^4$ oocysts of *E. necatrix* (NA 29₇+6) and group 4 was given $5 \times 10^4$ oocysts of *E. necatrix* (H). Group 5 was not inoculated, the chickens were weighed individually and assigned to the groups one day before inoculation (day −1) and then re-weighed 4, 6, 7, 8, 11 and 14 days after inoculation. The results obtained are given in the accompanying diagram FIG. 2, each value being the mean determined from observations on the 30 chickens (or survivors) in each group. No chickens given oocysts of *E. necatrix* (NA 36₇) died, and throughout the duration of the experiment there were no significant differences between the weight gains of groups 1 and 2 and the non-infected control group 5. (The weight gains of groups 1 and 2 given $5 \times 10^4$ and $2 \times 10^5$ oocysts of *E. necatrix* (NA 36₇), respectively, were identical and thus results for group 1 alone are shown.)

Severe coccidiosis resulted from inoculation of $5 \times 10^4$ oocysts of both *E. necatrix* (NA 29₇+6) and *E. necatrix* (H) and the mortality rates were 10% (3/30) and 60% (18/30) respectively. The weight gains of these chickens were severely retarded with the greatest effect being associated with *E. necatrix* (H) infection.

Lesion Scores

Groups of 10, 3-weeks-old chickens were inoculated with $5 \times 10^4$ oocysts of either *E. necatrix* (H), *E. necatrix* (NA 36₇) or *E. necatrix* (NA 29₇+6) or $2 \times 10^5$ oocysts of *E. necatrix* (NA 36₇). Six days later the chickens were killed and the intestinal lesions scored. No lesions were associated with *E. necatrix* (NA 36₇) infection, whereas all chickens given *E. necatrix* (H) died (lesion score of 4) and those given *E. necatrix* (NA 29₇+6) showed a mean lesion score of 3.15. The results obtained are given more fully in Table 7 below.

TABLE 7

Lesion scores associated with infections of *E. necatrix* (H) *E. necatrix* (NA 36₇) and *E. necatrix* (NA 29₇ + 6)

| Parasite and dose of oocysts given | \multicolumn{9}{c}{Numbers of chickens showing a lesion score of:-} | | | | | | | | |
|---|---|---|---|---|---|---|---|---|---|
| | 0 | $\frac{1}{2}$ | 1 | 1$\frac{1}{2}$ | 2 | 2$\frac{1}{2}$ | 3 | 3$\frac{1}{2}$ | 4 |
| *E. necatrix* (H) ($5 \times 10^4$) | 0 | 0 | 0 | 0 | 0 | 0 | 0 | 0 | 10 |
| *E. necatrix* (NA 36₇) ($5 \times 10^4$) | 10 | 0 | 0 | 0 | 0 | 0 | 0 | 0 | 0 |
| *E. necatrix* (NA 36₇) ($2 \times 10^5$) | 10 | 0 | 0 | 0 | 0 | 0 | 0 | 0 | 0 |
| *E. necatrix* (NA 29₇ + 6) ($5 \times 10^4$) | 0 | 0 | 0 | 0 | 0 | 5 | 0 | 2 | 3 |

Reproduction of *E. necatrix* (H), (NA 23₇), (NA 29₇), (NA 33₇) and (NA 36₇) in chickens To compare the reproductive potential of the parasites, groups of 15 chickens (three sub-groups of 5) were given either $5 \times 10^3$ oocysts of *E. necatrix* (H) or $25 \times 10^3$ or $1 \times 10^5$ oocysts of the egg-attenuated lines. Oocyst production was measured daily between 6 and 13 days after inoculation and the results obtained are given in Table 8 below.

TABLE 8

Reproduction of *E. necatrix* (H), (NA 23₇), (NA 29₇), (NA 33₇) and (NA 36₇) in chickens

| Parasite | Dose of oocysts given ($\times 10^{-3}$) | \multicolumn{4}{c}{Mean number of oocysts produced per bird ($\times 10^{-6}$)} | | | |
|---|---|---|---|---|---|
| *E. necatrix* (H)+ | 5 | 30.90 | 25.51 | 26.33 | 23.73 |
| *E. necatrix* (NA 23₇) | 25 | 1.29 | | | |
| | 100 | 1.69* | | | |
| *E. necatrix* (NA 29₇) | 25 | | 1.34 | | |
| | 100 | | 3.30 | | |
| *E. necatrix* (NA 33₇) | 25 | | | 0.56 | |
| | 100 | | | 1.84 | |
| *E. necatrix* (NA 36₇) | 25 | | | | 0.04 |
| | 100 | | | | 0.87 |

+included for each experiment as an internal standard
*2 birds died from coccidiosis Very few oocysts were produced following inoculation with *E. necatrix* (NA 36₇) even when the infective dose contained $1 \times 10^5$ oocysts. The peak of oocyst production for *E. necatrix* (NA 36₇) and *E. necatrix* (H) occurred between 6 and 8 and 10 days after inoculation, respectively.

Immunogenicity of *E. necatrix* (NA 29₇) in chickens maintained in litter pen isolators In an experiment similar to that described previously for *E. necatrix* (NA 22₇) the immunogenicity of *E. necatrix* (NA 29₇) was determined. Six groups of 30, 3-weeks-old chickens kept in litter pen isolators were used. Two groups of chickens were given a primary infection of $5 \times 10^3$ oocysts of *E. necatrix* (NA 29₇), two groups a primary infection of $1 \times 10^2$ oocysts of *E. necatrix* (H) and the remaining two groups were left uninfected. Subsequently all groups were challenged with a dose of $5 \times 10^4$ oocysts per chicken of *E. necatrix* (H). The body weights of all chickens were measured at the times of primary infection (day 0), at challenge (day 41) and 7 days after challenge (day 48); all chickens being killed at this latter time and their lesions graded. During the period of immunisation, litter in the isolators was sprayed with water 11 times between 8 and 24 days after primary infection to provide conditions favourable for the recycling of parasites. The results which were obtained are given below in Table 9 showing that the dose of $5 \times 10^3$ oocysts provides adequate protection against subsequent challenge with the parent pathogenic strain.

Two of the chickens given a primary infection of *E. necatrix* (H) died as a result of acute coccidiosis between 17 and 19 days after inoculation, but there were no deaths associated with primary infection with *E. necatrix* (NA 29₇).

Chickens given primary infections of *E. necatrix* (H) were completely immune to subsequent challenge as judged by body weight gain and lesion score. Some lesions were observed in chickens given *E. necatrix* (NA 29₇) primary infection, but changes in body weight gain were not significantly different from those of the control group. In contrast, unimmunised birds had severe lesions as a result of challenge (two birds died) and the weight gain was significantly depressed ($P<0.001$) compared with the control group.

PI. The prepatent period after 15 passages of the parent (H) strain was found to be 89 h.

Characteristics of the precocious line

1. Reproduction

The reproduction of the HP line was examined after the 12th passage (10 passages followed by 2 passages of relaxed selection pressure). Four groups of 3-weeks-old LS chickens were inoculated with doses of $1 \times 10^2$ or $1 \times 10^4$ oocysts per bird of either *E. acervulina* (H), or *E. acervulina* (HP), and the oocyst production of each group during the period from 3 to 9 days after inoculation was determined. The results obtained are given below in Table 10.

TABLE 9

Body weight changes of chickens given *E. necatrix* (H) and (NA29) and maintained in litter pen isolators

| Group No. | Parasite and dose of oocysts given for immunisationψ | Initial body weight (g) day 0 | Weight gain (g) day 0 to day 42 | Challenged with $5 \times 10^4$ oocysts of *E. necatrix* (H) | Weight gain (g) day 42 to day 49 | Mean intestinal lesion score 7 days after challenge |
|---|---|---|---|---|---|---|
| 1 | *E. necatrix* (NA29) $5 \times 10^3$ | 161.1 | 772.3 | YES | 144.1 | 0.4 |
| 2 | *E. necatrix* (NA29) $5 \times 10^3$ | 161.1 | 767.2 | NO | 175.6 | |
| 3 | *E. necatrix* (H) $1 \times 10^2$ | 161.3 | 694.1+ | YES | 163.4 | 0.0 |
| 4. | *E. necatrix* (H) $1 \times 10^2$ | 161.7 | 680.6 | NO | 165.0 | |
| 5. | None | 161.4 | 751.9 | YES | 6.4*** | 2.6 (two birds died) |
| 6. | None | 161.1 | 678.8φ | NO | 140.1 | |

+Two birds in this group died from infection with *E. necatrix*
φA 'leak' occurred in this isolator and large numbers of oocysts of *E. acervulina* were seen during the regular monitoring of litter up to day 42.
ψLitter sprayed with water 11 times during period of immunisation.
***Significantly different from groups 1, 2, 3, 4 and 6 ($P<0.001$)

EXAMPLE 3

An attenuated line of *E. acervulina* has also been developed by selection for precocious development of coccidia grown in chickens. This precocious, "attenuated" line hereinafter referred to as the (HP) line of *E. acervulina* may be incorporated with egg attenuated *E. necatrix* (NA), as described in previous examples, into vaccines for combatting and controlling chicken coccidiosis of poultry, according to a preferred embodiment of the invention.

Development of the precocious, "attenuated" strain *E. acervulina* (HP)

In a preliminary experiment the prepatent period of the parent pathogenic Houghton (H) strain of *E. acervulina* was found to be 89 h as determined by salt flotations of faecal samples taken at intervals of one hour.

In order to develop a precocious line, therefore, oocysts were initially recovered 96 h post infection (PI), and thereafter the first oocysts produced were inoculated into further chickens (LS) and within 2 passages the prepatent period had been reduced to 83 h. Some difficulty was experienced at the 4th passage in collecting sufficient oocysts at 83 h but, subsequently, it proved possible to reduce the time required to collect workable numbers of oocysts to 72 h. At this latter stage it was necessary to relax the selection pressure for precocious development after 2 unsuccessful attempts to reduce further the collection time, and oocysts were collected after 90 h. The earlist time after infection at which it was possible to collect oocysts was 70 h, at the 14th passage.

Parallel chicken passages of the parent pathogenic strain were carried out, oocysts being collected 120 h

TABLE 10

The total mean oocyst output over 9 days per LS chicken given either $1 \times 10^2$ or $1 \times 10^4$ oocysts of *E. acervulina* (H) or (HP)

| Strain and dose of oocysts given | Mean oocyst output per bird ($\times 10^{-6}$) |
|---|---|
| (H) $1 \times 10^2$ | 11.9 |
| (H) $1 \times 10^4$ | 299.5 |
| (HP) $1 \times 10^2$ | 1.7 |
| (HP) $1 \times 10^4$ | 119.0 |

Up to the ninth day after infection the parent (H) strain produced numbers of oocysts which were greater than those produced by the precocious line by factors of 6.9 and 2.5 for inoculations of $1 \times 10^2$ and $1 \times 10^4$ oocysts respectively.

2. Histology

Endogenous stages of (HP) line and the (H) strain were studied in stained sections of intestine. It was found that development of the endogenous strains of the two parasites was identical up to 60 h PI. At 66 h PI, however, gametocytes were found in the (HP) line infection, but did not appear in the parent (H) strain infection until 80 h. A few mature 4th generation schizonts were seen in infections with both parasites at 66 h but subsequently were abundant only in association with the (H) strain. It appears, therefore, that gametocytes of the (HP) line develop mainly from 3rd generation schizonts with a small number developing later from 4th generation schizonts.

Pathogenicity and Immunogenicity

1. Pathogenicity

Figure 3:
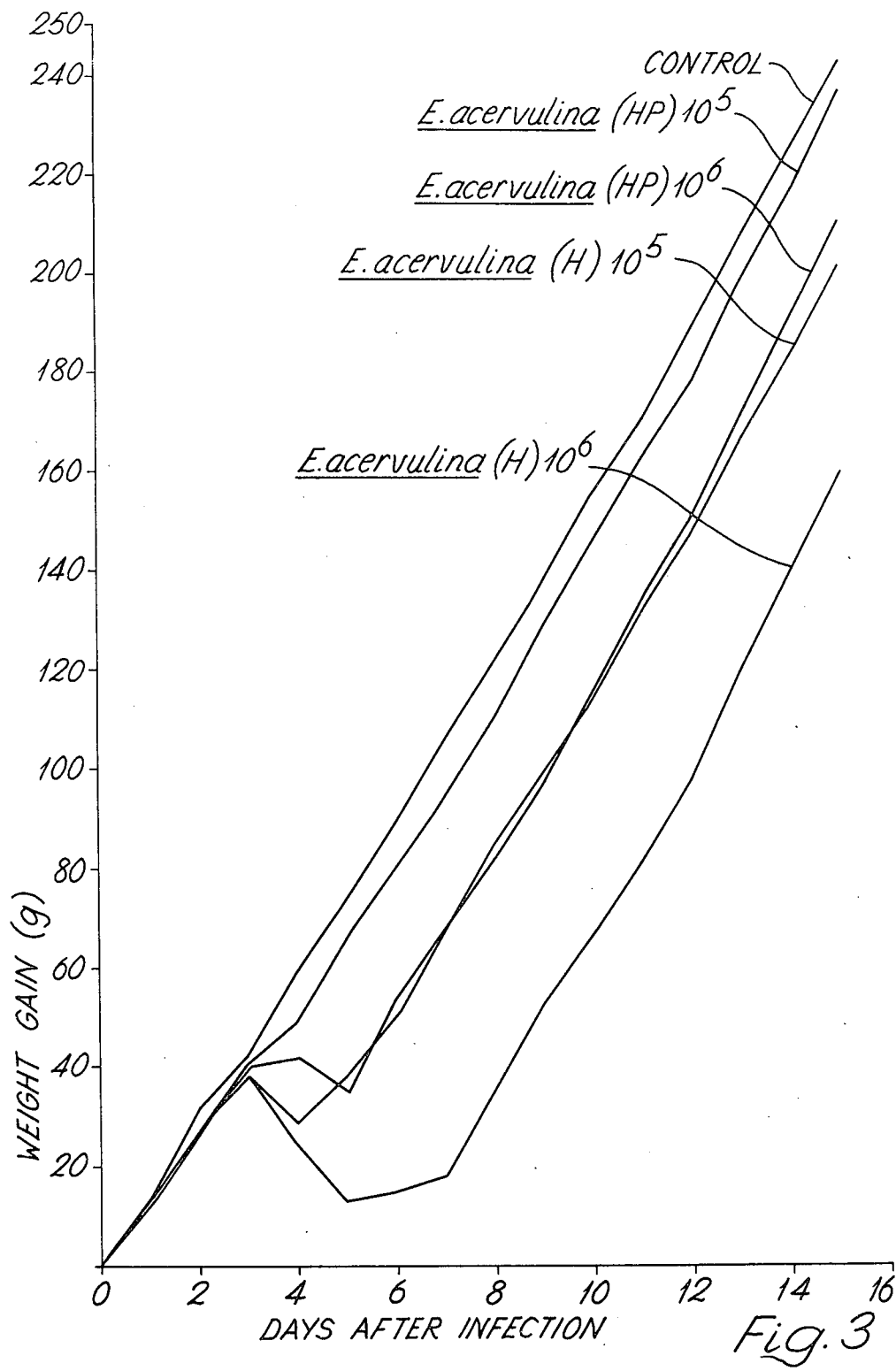

As in previous examples for *E. necatrix*, the pathogenicity of *E. acervulina* (H) and (HP) was measured by comparing the weight gains of uninfected and infected birds. Birds were weighed individually each day from the day before infection until the 14th day after infection and the mean weight gains were calculated. *E. acervulina* (HP) oocysts used in this experiment were obtained after the 13th passage (10 passages followed by 3 passages of relaxed selection pressure). Five groups of 3-weeks-old weight-matched LS chickens (each group divided into 3 sub-groups of 7) were used; four groups being given $1 \times 10^5$ or $1 \times 10^6$ oocysts per chicken of either the (H) strain or the (HP) line; and the remaining group being kept as an uninfected control group. The results obtained are given diagrammatically in FIG. 3 showing that the weight losses of birds infected with *E. acervulina* (HP) were significantly (P<0.001) less than for the (H) strain infected birds. Birds given $1 \times 10^5$ oocysts of the (HP) line showed no mean weight loss while birds given the same dose of the (H) strain lost weight on day 5 after challenge. The higher dose ($10^6$ oocysts) of the (H) strain and (HP) line both produced weight loss, though chickens given the (HP) line recovered significantly faster. Four chickens (19%) given the higher dose of the (H) strain died, whilst no birds given the oocysts of the (HP) line died.

2. Immunogenicity

Oocysts of the (HP) line from the 12th passage (10 passages followed by 2 passages of relaxed selection pressure) were used for this experiment. Four groups of 3-weeks-old LS birds (each group made up of 3 sub-groups of 4 birds) were given $1 \times 10^5$ oocysts per bird of the (H) strain or (HP) line and challenged 14 days later with $1 \times 10^3$ oocysts per bird of either parasite. At the time of challenge 2 control groups were also given $1 \times 10^3$ oocysts of either parasite. The results obtained are given below in Table 11, indicating that chickens given a primary infection of the (HP) line were almost completely immune to challenge with the (H) strain as judged by their oocyst output. These birds were also strongly immune to subsequent challenge with the (HP) line. These results indicate that, despite a reduction in the reproductive capacity of the (HP) line, it is still characterised by stages which contain the antigens responsible for protective immunity.

TABLE 11

| Cross-immunity between the (H) strain and (HP) line of *E.acervulina* in LS chickens | | |
|---|---|---|
| Immunising parasite ($1 \times 10^5$ oocysts) | Challenge parasite ($1 \times 10^3$ oocysts) | Oocysts/bird days 4–8 ($\times 10^{-6}$) |
| H | H | 0.06 |
| HP | HP | 0.1 |
| HP | H | 6.65 |
| — | H | 352.9 |
| — | HP | 56.8 |

Attenuated, precocious lines of *E. acervulina* (HP), such as those described above may be incorporated with the egg-attenuated lines of *E. necatrix* (NA) of the invention in vaccines for prevention and control of coccidiosis in chickens.

I claim:

1. A process for the production of an attenuated strain of *E. necatrix*, which comprises:
    passaging a pathogenic *E. necatrix* in embryonated eggs for from about 20 to about 60 passages.

2. A process according to claim 1, in which embyronated eggs are inoculated with sporozoites of *E. necatrix* and oocysts are subsequently removed from said eggs, and in which during the first n egg passages, where n is a number from 6 to 10, alternate passages are carried out in eggs and chickens.

3. A process according to claim 1, in which conditions used during in ovo culture include the use of a temperature of from 39° to 43° C. and turning of the eggs at least once per day.

4. A process according to claim 1, in which the selection pressures comprise selection for precocious development.

5. A process according to claim 1, in which passaging is carried out in the chorioallantoic membrane of embryonated eggs; sporozoites of *E. necatrix* are inoculated into said membrane; conditions used during in ovo passaging include the use of a temperature of from 39° to 43° C. and turning of the eggs at least once per day; during the first n egg passages, where n is a number from 6 to 10, alternate egg passages are carried out in eggs and chickens; from 20 to 50 egg passages are used; and oocysts are recovered from the eggs.

6. A process according to claim 1, in which from about 30 up to about 50 egg passages are used when selection pressures are relaxed during passaging.

7. A process according to claim 1, in which selection pressures are imposed during passaging and from about 20 up to about 40 egg passages are used.

8. A vaccine for the prevention and control of coccidiosis in poultry, which comprises:
    a live attenuated strain of *E. necatrix* produced by passaging a pathogenic *E. necatrix* strain in embryonated eggs for from about 20 to about 60 passages.

9. A vaccine according to claim 8, further comprising food or drinking water.

10. A method for the prevention and control of coccidiosis in poultry, in which poultry are vaccinated with a vaccine according to claim 8.

11. A vaccine according to claim 8, further comprising at least one other attenuated non-pathogenic strain of Eimeria in addition to *E. necatrix*.

12. A vaccine according to claim 8, further comprising at least one attenuated, precocious strain of Eimeria.